(12) United States Patent
Kim et al.

(10) Patent No.: US 9,024,063 B2
(45) Date of Patent: May 5, 2015

(54) METHOD FOR INCREASING METHIONINE PRODUCTIVITY USING A MIXTURE OF METHYL MERCAPTAN AND DIMETHYL SULFIDE

(75) Inventors: So Young Kim, Gwacheon-si (KR); Yong Uk Shin, Yongin-si (KR); In Kyung Heo, Gangseo-gu (KR); Hyun Ah Kim, Namwon-si (KR); Ju Eun Kim, Seoul (KR); Chang Il Seo, Incheon (KR); Sung Kwang Son, Seoul (KR); Sang Mok Lee, Seoul (KR); Sung Hoo Jhon, Seoul (KR); Han Jin Lee, Seoul (KR); Kwang Ho Na, Gangseo-gu (KR); Il Chul Kim, Seongnam-si (KR)

(73) Assignee: CJ Cheiljedang Corporation, Seoul (KR)

( * ) Notice: Subject to any disclaimer, the term of this patent is extended or adjusted under 35 U.S.C. 154(b) by 919 days.

(21) Appl. No.: 13/203,521

(22) PCT Filed: Feb. 26, 2010

(86) PCT No.: PCT/KR2010/001250
§ 371 (c)(1),
(2), (4) Date: Nov. 4, 2011

(87) PCT Pub. No.: WO2010/098629
PCT Pub. Date: Sep. 2, 2010

(65) Prior Publication Data
US 2012/0123158 A1   May 17, 2012

(30) Foreign Application Priority Data
Feb. 27, 2009   (KR) .................. 10-2009-0016604

(51) Int. Cl.
*C12P 13/12* (2006.01)
*C07C 323/58* (2006.01)

(52) U.S. Cl.
CPC ..................................... *C12P 13/12* (2013.01)

(58) Field of Classification Search
None
See application file for complete search history.

(56) References Cited

U.S. PATENT DOCUMENTS

| 2,775,616 A * | 12/1956 | Holland et al. ............... 562/559 |
| 2008/0194030 A1 | 8/2008 | Park et al. |
| 2010/0184164 A1 | 7/2010 | Kim et al. |

FOREIGN PATENT DOCUMENTS

| KR | 10-2006-0000774 A | 1/2006 |
| KR | 10-2008-0011132 A | 1/2008 |
| KR | WO 2008-013432 A1 | 1/2008 |
| KR | 10-2008-0033413 A | 4/2008 |
| KR | 10-2008-0102123 A | 11/2008 |
| WO | WO 2007-011939 A2 | 1/2007 |

OTHER PUBLICATIONS

International Search Report (ISR) for PCT/KR2010/001250, I.A. fd: Feb. 26, 2010, mailed Oct. 14, 2010 from the Korean Intellectual Property Office, Daejeon, Republic of Korea (english translation only).
International Preliminary Report on Patentability (Chapter I of the Patent Cooperation Treaty) for PCT/KR2010/001250, I.A. fd: Feb. 26, 2010, issued Oct. 25, 2011 from the International Bureau of WIPO, Genera, Switzerland.
Jeon, B-R et al., S-Adenosylmethionine protects post-ischemic mitochondrial injury in rat liver, *J Hepatology* 34(3):395-401 (Mar. 2001), Elsevier, Oxford, England.

* cited by examiner

*Primary Examiner* — Michael Barker
*Assistant Examiner* — Po-Chih Chen
(74) *Attorney, Agent, or Firm* — Sterne, Kessler, Goldstein & Fox P.L.L.C.

(57) ABSTRACT

The present invention relates to a method for increasing L-methionine productivity and organic acid productivity. More particularly, the present invention relates to a method which involves adding a mixture containing methyl mercaptan and dimethyl sulfide at a appropriate ratio to O-acetyl homoserine or O-succinyl homoserine and to an enzyme having an activity of converting methionine precursor into L-methionine, so as to perform an enzyme reaction, to thereby improve the conversion rate of L-methionine and organic acid from the L-methionine precursor, and thus increasing L-methionine yield as compared to conventional method.

9 Claims, 2 Drawing Sheets

METHOD FOR INCREASING METHIONINE PRODUCTIVITY USING A MIXTURE OF METHYL MERCAPTAN AND DIMETHYL SULFIDE

BACKGROUND OF THE INVENTION

1. Field of the Invention

The present invention relates to a method for improving productivity of L-methionine and organic acid.

2. Description of the Related Art

Methionine is one of the essential amino acids in the body, and has been widely used as an animal feed and food additive, as well as a component of medical aqueous solutions and other raw material for medicinal products. Methionine acts as a precursor of choline (lecithin) and creatine, and is also used as a raw material for the synthesis of cysteine and taurine. In addition, it functions as a sulfur donor. S-adenosyl-methionine is derived from L-methionine and serves as a methyl donor in the body, and it is involved in the synthesis of various neurotransmitters in the brain. Methionine and/or S-adenosyl-L-methionine (SAM) is/are also found to prevent lipid accumulation in the liver and arteries and to be effective for the treatment of depression, inflammation, liver diseases and muscle pain (Jeon B R et al., J. Hepatol., 2001 March; 34(3): 395-401).

For the chemical synthesis of methionine, L-methionine is produced through the hydrolysis of 5-(β-methylmercaptoethyl)-hydantoin. However, the chemically synthesized methionine is disadvantageously present in a mixture of L- and D-forms. Therefore, the present inventors developed a biological method for selectively synthesizing L-methionine, and have already applied for a patent (WO 2008/103432). The method, is termed briefly as "a two-step process", comprises the fermentative production of an L-methionine precursor and the enzymatic conversion of the L-methionine precursor to L-methionine. The L-methionine precursor preferably includes O-acetyl homoserine and O-succinyl homoserine. The two-step process is evaluated in terms of having overcome the problems from which the conventional methods suffer, such as sulfide toxicity, feedback regulation of strain by methionine and SAMe, and degradation of intermediates by cystathionine gamma synthase, O-succinyl homoserine sulfhydrylase and O-acetyl homoserine sulfhydrylase. Also, compared to the conventional chemical synthesis method of producing D- and L-methionine, the two-step process has the advantage of being selective for L-methionine only, with the concomitant production of organic acids, more particularly, succinic acid and acetic acid as useful by-products. The succinic acid is used as a raw material of paints, cosmetics, or medicinal products, and acetic acid is very useful in industrial fields, including preparation of vinyl acetic acid, staining, medicinal products such as aspirin, and photographic fixing solutions.

In the enzymatic conversion reaction of the two-step process, enzymes which have the activities of cystathionine gamma synthase, O-succinyl homoserine sulfhydrylase and O-acetyl homoserine sulfhydrylase are used, and O-acetyl homoserine or O-succinyl homoserine as the L-methionine precursor is mixed with methyl mercaptan to produce L-methionine and an organic acid by enzymatic reaction.

Methyl mercaptan exists as a gas at room temperature, and is slightly soluble in water, and has a high solubility in alkaline solutions. The enzymatic conversion reaction for L-methionine production occurs in an aqueous solution. Thus, if methyl mercaptan has a more improved solubility in the aqueous solution, it is expected to greatly increase methionine productivity.

Considering the above problem, the present inventors have made an effort to increase the solubility of methyl mercaptan in the enzymatic conversion reaction for maximization of L-methionine production. As a result, they found that a mixture of methyl mercaptan and dimethyl sulfide mixed at a appropriate ratio can improve the conversion rate of L-methionine and organic acid from L-methionine precursor, and thus L-methionine can be produced in a high yield, compared to the conventional methods, thereby completing the present invention.

SUMMARY OF THE INVENTION

It is an object of the present invention to provide a method for improving the conversion rate from the L-methionine precursor, O-acetyl homoserine or O-succinyl homoserine to the L-methionine, by using the mixture of a sulfur compound, dimethyl sulfide and the methyl mercaptan, which is another sulfur compound used as a substrate in an enzymatic conversion reaction.

Effect of the Invention

By using the method of the present invention, the production rate and purity of L-methionine and organic acid can be increased compared to the single use of methyl mercaptan during the conversion reaction. Moreover, economic benefits of saving cost for reaction facility can be obtained by the improved methionine productivity.

DETAILED DESCRIPTION OF THE PREFERRED EMBODIMENTS

Figure 1:
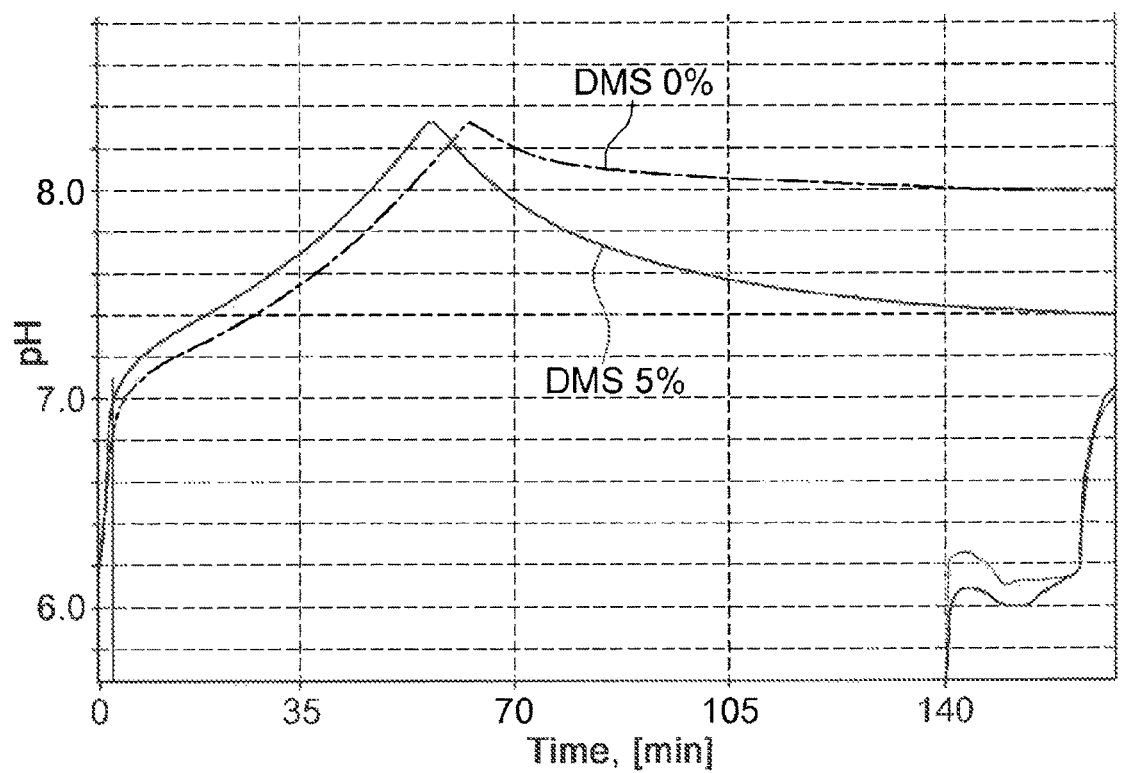
FIG. 1 is a graph of pH change showing the rate of enzymatic conversion reaction according to the supply of a methyl mercaptan solution or a mixture of methyl mercaptan and dimethyl sulfide solution in a 1 L batch reactor.

In order to achieve the above object, an aspect of the present invention is to provide a method for producing methionine, comprising:

1) preparing a reaction solution that includes a methionine precursor which is an O-acetyl homoserine or an O-succinyl homoserine, an enzyme which has the activity of converting the methionine precursor into methionine, and a mixture of methyl mercaptan and dimethyl sulfide; and 2) performing an enzymatic conversion reaction while stirring the reaction solution.

The term "two-step process", as used herein, refers to a method for producing L-methionine disclosed in WO2008/013432, comprising the steps of producing O-acetyl homoserine or O-succinyl homoserine by glucose fermentation using a fermentation strain prepared according to the method; and converting O-acetyl homoserine or O-succinyl homoserine, together with methyl mercaptan, into methionine by enzymatic conversion, thereby producing L-methionine.

Hereinafter, the present invention will be described in detail.

An aspect of the present invention is to provide a method for producing methionine, comprising:

1) preparing a reaction solution that includes a methionine precursor which is an O-acetyl homoserine or an O-succinyl homoserine, an enzyme which has the activity of converting the methionine precursor into methionine, and a mixture of methyl mercaptan and dimethyl sulfide; and 2) performing an enzymatic conversion reaction while stirring the reaction solution.

The stirring of step 2) may be performed at 500 to 1000 rpm, preferably 600 to 900 rpm, and more preferably 700 to 800 rpm.

The method of the present invention may further comprise terminating the enzymatic conversion reaction, and in the specific embodiment of the present invention, 2N HCl is used to terminate the reaction.

In addition, the method of the present invention may further comprise purification of methionine presented in the reaction solution. In particular, methionine purification step may comprise:

1) separating the microorganism from the enzymatic conversion reaction solution;

2) decoloring and filtering the reaction solution, of which the microorganism is removed; and 3) crystallizing from the filtrate.

The step of separating the microorganism may be performed using a high speed centrifuge or a membrane filter. The step of decoloring and filtering the microorganism-removed solution may be performed using an activated carbon, but is not limited thereto.

In the two-step process for producing methionine, methionine is produced by enzymatic conversion reaction using O-acetyl homoserine or O-succinyl homoserine as an L-methionine precursor and methyl mercaptan (CH$_3$SH) as substrates (WO2008/013432). In this regard, methyl mercaptan is used as a sulfur source which can react with the substrate, O-acetyl homoserine or O-succinyl homoserine to produce methionine, and thus the production efficiency of methionine may be greatly affected by the reactivity of methyl mercaptan. However, methyl mercaptan has a very low solubility in a neutral aqueous solution, and is volatile and thus quickly evaporated from the solution. Therefore, if a method capable of improving the reactivity of methyl mercaptan is developed, the maximum amount of methyl mercaptan as possible can react before the evaporation of methyl mercaptan, so as to improve the production yield of methionine. Accordingly, the present inventors intended to improve the reactivity of methyl mercaptan by the addition of another material to the reaction solution containing methyl mercaptan. As a result, they found that when dimethyl sulfide (DMS) as another material is mixed with methyl mercaptan to induce the reaction, the conversion rate can be increased.

In the specific Example of the present invention, the conversion reaction does not occur when dimethyl sulfide is used alone. However, when the mixture of methyl mercaptan with dimethyl sulfide is used, the conversion rate is increased, compared to the single use of methyl mercaptan (see Tables 1 and 4, and FIG. 2). In addition, the reaction rate of enzyme was higher than that of the single use of methyl mercaptan, according to the rate of pH decline by acetic acid, which is a by-product produced by mixing with dimethyl sulfide (see FIG. 1). Moreover, when a continuous supply of the mixture is performed (see Table 2) or a large-scale culture is performed (see Table 3), the conversion rates were also improved, compared to the single use of methyl mercaptan. Accordingly, the method of the present invention can be effectively used to improve the conversion rate of L-methionine from O-acetyl homoserine or O-succinyl homoserine.

The conversion reaction of methionine from methionine precursor using enzymes having an activity converting into methionine is as shown in the following Reaction Schemes.

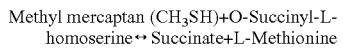
Methyl mercaptan (CH$_3$SH)+O-Succinyl-L-homoserine ↔ Succinate+L-Methionine

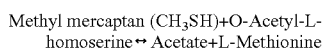
Methyl mercaptan (CH$_3$SH)+O-Acetyl-L-homoserine ↔ Acetate+L-Methionine In the above Reaction Schemes, the CH$_3$S— residue of methyl mercaptan is substituted with the succinate or acetate residue of O-succinyl homoserine or O-acetyl homoserine to produce methionine.

Upon the reaction, methyl mercaptan (CH$_3$SH) may be added in a variety of forms. Preferably, methyl mercaptan may be added in a form of methyl mercaptan gas or sodium methyl mercaptan solution may be also used as a liquid type, because the sodium methyl mercaptan solution and methyl mercaptan gas show the same reaction properties in an aqueous reaction solution. Therefore, the methyl mercaptan may be used directly, or in a form of sodium methyl mercaptan solution by solubilizing it in a sodium hydroxide solution. However, since methyl mercaptan exists as a gas at room temperature, it is more preferable to use the sodium methyl mercaptan solution prepared by solubilizing methyl mercaptan in a sodium hydroxide solution.

In the present invention, the enzyme which has an activity of converting into methionine may include one or more selected from the group consisting of cystathionine gamma synthase, O-succinyl homoserine sulfhydrylase, and O-acetyl homoserine sulfhydrylase.

In the above reaction, the enzymes having an activity of converting into methionine used in the production of methionine may be those derived from a microorganism strain belonging to *Escherichia* sp., *Pseudomonas* sp., *Leptospira* sp., *Corynebacterium* sp., *Saccharomyces* sp., *Chromobacterium* sp., *Nocardia* sp., *Bradyrhizobium* sp., *Hyphomonas* sp., *Methylococcus* sp., *Methylobacillus* sp., *Nitrosomonas* sp., *Klesiella* sp., *Bacillus* sp., *Shigella* sp., *Colwellia* sp., *Salmonella* sp., yeast, or fungi.

In the above conversion reaction, when O-succinyl homoserine is used as a substrate, the enzyme may include one or more selected from the group consisting of cystathionine gamma synthase, O-succinyl homoserine sulfhydrylase and O-acetyl homoserine sulfhydrylase, which are preferably derived from microorganism strains belonging to *Pseudomonas* sp., *Nocardia* sp., and *Chromobacterium* sp., and more preferably derived from microorganism strains belonging to *Pseudomonas aurogenosa, Nocardia Farcinica, Pseudomonas putida*, and *Chromobacterium Violaceum*.

In the above conversion reaction, when O-acetyl homoserine is used as a substrate, the enzyme may include one or more selected from the group consisting of cystathionine gamma synthase, O-succinyl homoserine sulfhydrylase and O-acetyl homoserine sulfhydrylase, which are preferably derived from microorganism strains belonging to *Leptospira* sp., *Corynebacterium* sp., and *Hyphomonas* sp., and more preferably derived from microorganism strains belonging to *Leptospira meyeri, Pseudomonas aurogenosa, Hyphomonas Neptunium*, and *Corynebacterium Violaceum*.

In the specific embodiment of the present invention, O-acetyl homoserine or O-succinyl homoserine that is used as a substrate in the conversion reaction for the production of L-methionine was produced by fermentation of the microorganism strain prepared according to the method described in WO2008/013432, and the substrate, O-acetyl homoserine or O-succinyl homoserine was purified from the fermented solution by methanol precipitation.

Further, the enzymes used in the conversion reaction for the production of L-methionine were obtained from the genes of O-succinyl homoserine sulfhydrylase derived from *Chromobacterium violaceum* and O-acetyl homoserine sulfhydrylase derived from *Hyphomonas Neptunium*, in which the strains containing the genes were fermented, recovered and then disrupted according to the method described in WO2008/013432.

The conversion reaction solution was prepared by mixing O-acetyl homoserine or O-succinyl homoserine, which was the substrate recovered by the above method, together with the enzyme which has an activity of converting into methionine.

The other substrate, methyl mercaptan was mixed with dimethyl sulfide at a appropriate ratio, and added to the conversion reaction solution, and the conversion rates of methionine from O-acetyl homoserine or O-succinyl homoserine was compared in each case. The results showed that a mixing ratio of methyl mercaptan and dimethyl sulfide was optimal when the methyl mercaptan:dimethyl sulfide ratio was 1:0.05 (mol:mol) to 1:1 (mol:mol), preferably 1:0.20 (mol:mol) to 1:1 (mol:mol), and more preferably 1:0.25 (mol:mol) to 1:0.5 (mol:mol). Meanwhile, dimethyl sulfide is preferably used at a ratio of 5% to 25%, and more preferably 20% to 25%, based on the molar concentration of methyl mercaptan.

Another aspect of the present invention is to provide methionine prepared by the above method.

The methionine may be in a dried powdery form or in a liquid form dissolved in an aqueous solution, which is purified by a purification process.

The method of converting L-methionine precursor into L-methionine using the mixture of methyl mercaptan and dimethyl sulfide according to the present invention is able to produce L-methionine at a higher yield than the conventional methods, and thus the produced methionine can be applied to various fields including animal feeds, food additives, medicines, and other raw materials for medicinal products.

Hereinafter, constitutions and effects of the present invention will be described in more detail with reference to Examples. However, these Examples are for illustrative purposes only, and the invention is not intended to be limited by these Examples.

Example 1

Comparison of Conversion Rate of Methionine from O-Acetyl Homoserine According to Mixing Ratio of Methyl Mercaptan and Dimethyl Sulfide Upon conversion reaction, dimethyl sulfide was mixed with a methyl mercaptan solution at a appropriate ratio, and the mixture was added to a conversion reaction solution so as to examine the conversion rate of methionine from O-acetyl homoserine.

Methyl mercaptan exists as a gas at room temperature, and may exist in a form of sodium methyl mercaptan solution (sodium methyl mercaptan, $CH_3S-Na$, 2.14 M, 15%, Tokyo chemical industry, Japan) by adding it to a sodium hydroxide solution. In the present Example, a 2.14 M sodium methyl mercaptan solution was used to perform the experiment. Hereinbelow, the 2.14 M sodium methyl mercaptan solution will be designated as a methyl mercaptan solution. The methyl mercaptan solution and dimethyl sulfide solution (13.38 M, 99%, arkema, France) were mixed at a appropriate molar ratio (mol:mol), and stirred to prepare a mixed solution.

The conversion reaction solution was prepared by adding 50 µl of converting enzyme solution and 0.1 mM pyridoxal 5'-phosphate (Sigma, USA) as a cofactor to 1 ml of O-acetyl homoserine solution (500 mM). The O-acetyl homoserine solution was prepared by dissolving O-acetyl homoserine purified from a fermented liquid in a phosphate buffer solution (pH 7.5).

A CJM-BTJA/pCJ-metXlme-CL strain prepared by the method disclosed in WO2008/013432 was used as a fermentation strain. The CJM-BTJA/pCJ-metXlme-CL strain was inoculated in a 5 L fermenter, and cultivation was performed by fed batch fermentation for 50~100 hrs. O-acetyl homoserine was purified from the fermented liquid by methanol precipitation. The converting enzyme was obtained from *E. coli* W3110 strain transformed with pCJ-MetZ-CL derived from *Hyphomonas Neptunium*, in which the strain was fermented, and then recovered and disrupted according to the method disclosed in WO2008/013432. The mixture of methyl mercaptan and dimethyl sulfide was added to the prepared conversion reaction solution to initiate the enzyme reaction. In this regard, the added amount of the mixture of methyl mercaptan and dimethyl sulfide was adjusted until the final amount of methyl mercaptan became 0.04 mM. The reaction was performed at a temperature of 33° C. and 800 rpm for 10 min under stirring. For the termination of the reaction, a 0.2 N HCl solution was added to terminate the reaction. A concentration of the final product methionine was analyzed by HPLC. The analysis was performed under the conditions disclosed in WO2008/013432.

The conversion rate (%) of methionine from O-acetyl homoserine was calculated from a percentage (%) of the number of moles of the produced methionine to the number of moles of the substrate (mol/L) used in the reaction. When 1 mol of methionine was produced from 1 mol of O-acetyl homoserine and methyl mercaptan, the conversion rate (%) was regarded as 100%. The analysis results are shown in the following Table 1.

TABLE 1

Comparison of Conversion rates of O-acetyl homoserine between different mixing ratios of methyl mercaptan solution (SMM) and dimethyl sulfide (DMS)

| Molar ratio | | Met production amount | Conversion | Relative activity |
|---|---|---|---|---|
| SMM | DMS | [met-g]/[10 min] | rate (%) | (%) |
| 1 | 0 | 4.44 | 74.5 | 100 |
| 1 | 0.05 | 4.52 | 75.7 | 102 |
| 1 | 0.10 | 4.62 | 77.6 | 104 |
| 1 | 0.20 | 5.07 | 85.1 | 114 |
| 1 | 0.25 | 5.95 | 100 | 134 |
| 1 | 0.35 | 5.60 | 94.0 | 126 |
| 1 | 0.70 | 5.70 | 95.6 | 128 |
| 1 | 1.00 | 5.88 | 98.7 | 132 |

As shown in Table 1, when a mixture of methyl mercaptan solution and dimethyl sulfide was added at a ratio of 1:0.25 (mol:mol), the production of methionine was increased to 34%, compared to the single use of methyl mercaptan. When the mixing ratio of methyl mercaptan solution and dimethyl sulfide was increased to more than 1:0.25, the relative activity was not increased further, but was maintained at a high level.

As a control group, when dimethyl sulfide was only added to the conversion reaction solution in an amount identical to that contained in the 1:1 mixture of methyl mercaptan and dimethyl sulfide, the production of methionine was not observed, indicating that the single use of dimethyl sulfide cannot produce methionine. Therefore, it is suggested that dimethyl sulfide is mixed with methyl mercaptan to increase the reactivity of methyl mercaptan, thereby improving the production of methionine.

Example 2

Conversion Reaction of Methionine Using Mixture of Methyl Mercaptan and Dimethyl Sulfide To examine whether the improved production of methionine continuously occurs under the same conditions as in Example 1, the production of methionine was examined while the mixture of methyl mercaptan and dimethyl sulfide was continuously added according to time. The reaction was maintained using the same conversion reaction solution for 30 min while the methyl mercaptan solution and the mixture with dimethyl sulfide were added every 10 min. After 30 min, the reaction was terminated, and the amount of produced methionine was measured by HPLC. The reaction was performed under the condition of the mixing ratio of methyl mercaptan solution and dimethyl sulfide of 1:0.25 (mol:mol), at which the highest production of methionine was observed in Example 1. The results are shown in the following Table 2.

TABLE 2

Comparison of conversion rates according to continuous supply of methyl mercaptan solution or dimethyl sulfide mixture in 1.5 mL tube scale

|  | Methyl mercaptan solution (100%) | Mixture of Methyl mercaptan:Dimethyl sulfide (1:0.25 mix) |
| --- | --- | --- |
| Methionine [g/L] | 12.84 | 14.69 |
| Conversion rate [%] | 66.88 | 76.51 |
| Relative activity [%] | 100.00 | 114.41 |

As shown in Table 2, the conversion rate was increased to approximately 15% after 30 min, compared to the single use of methyl mercaptan.

Example 3

Enzymatic Conversion Reaction of O-Acetyl Homoserine in 1 L Batch Reactor

To examine the efficiency of conversion reaction in a large-scale reactor, the reaction was performed using 500 mL of 700 mM O-acetyl homoserine in a 1 L batch reactor. The enzymatic conversion reaction was performed while continuously supplying the methyl mercaptan solution or the mixture of methyl mercaptan and dimethyl sulfide of 1:0.25 (mol:mol) at a flow rate of 3.0 mL/min for 60 mM. The amount of methyl mercaptan contained in each solution was adjusted to be identical. The reaction temperature was 33° C. and the agitation was performed at 700 rpm. The converting enzyme liquid was prepared in the same manner as in the above Example, and 10 mL thereof was added. 0.1 mM pyridoxal 5'-phosphate (Sigma, USA) as a cofactor was added. After about 3 hrs, the amount of produced methionine was measured by HPLC. The results are shown in the following Table 3.

TABLE 3

Comparison of conversion rates according to supply of methyl mercaptan or dimethyl sulfide mixture in 1 L batch reactor

|  | SMM (100%) | SMM 1:DMS 0.25 (mol:mol) |
| --- | --- | --- |
| Methionine [g/L] | 65.6 | 75.5 |
| Conversion rate [%] | 85 | 100 |
| Relative activity [%] | 100 | 118 |

As shown in Table 3, when the mixture of methyl mercaptan solution and dimethyl sulfide was added at a ratio of 1:0.25 (mol:mol), the conversion rate was increased to approximately 18%, compared to the single use of methyl mercaptan.

Figure 2:
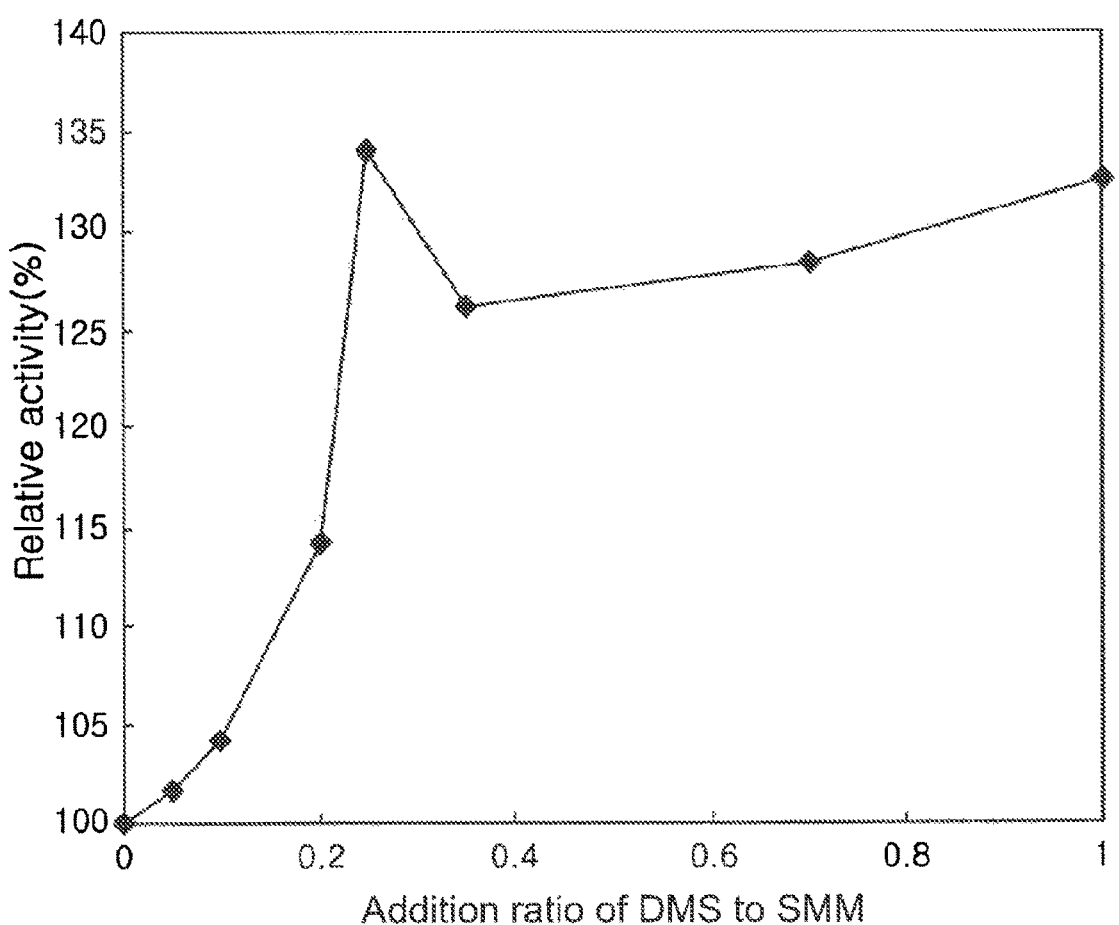
FIG. 2 is a graph showing relative activity according to the mixing ratio of methyl mercaptan solution (SMM) and dimethyl sulfide (DMS).

Upon the conversion reaction of O-acetyl homoserine, acetate was also produced as a product in addition to methionine, and thus pH drop occurred. After initiation of the reaction, while the methyl mercaptan solution and the mixture of methyl mercaptan and dimethyl sulfide were supplied, pH increased because methyl mercaptan was supplied in the liquid form by dissolving it in NaOH. However, after completion of the supply, pH decreased. When acetic acid (in the case of using O-acetyl homoserine as a substrate) or succinic acid (in the case of using O-succinyl homoserine as a substrate) was produced as the by-products of the conversion reaction, the reaction rate of enzyme can be reflected by the rate of pH decline. As shown in FIG. 1, when the mixture of methyl mercaptan and dimethyl sulfide of 1:0.25 (mol:mol) was used, the reaction rate of enzyme according to the rate of pH decline was found to be relatively high, compared to the single use of methyl mercaptan.

Example 4

Enzymatic Conversion Reaction of O-Succinyl Homoserine According to Addition Amount of Dimethyl Sulfide to Methyl Mercaptan O-succinyl homoserine was also used as a substrate for the enzymatic conversion reaction of methionine so as to perform the reaction of producing methionine and succinic acid.

The different amounts of dimethyl sulfide were added to the methyl mercaptan solution in 1.5 mL tube scale as in Example 1, and then the conversion rates of methionine from O-succinyl homoserine were compared. Dimethyl sulfide was added at a ratio of methyl mercaptan to dimethyl sulfide of 1:0, 1:0.25, 1:0.35, and 1:1 (mol:mol). The conversion reaction liquid was prepared by adding 50 µl of the converting enzyme liquid and 0.1 mM pyridoxal 5'-phosphate as a cofactor to 1 ml of O-succinyl homoserine solution (500 mM). The O-succinyl homoserine solution was prepared by dissolving O-succinyl homoserine purified from a fermented liquid in a phosphate buffer solution (pH 7.5). A CJM-BTJ/pCJ-metA-CL strain prepared by the method disclosed in WO2008/013432 was inoculated in a 5 L fermenter, and cultivation was performed by fed batch fermentation for 50~100 hrs. O-succinyl homoserine was purified from the fermented liquid by methanol precipitation. The converting enzyme was obtained from *E. coli* W3110 strain transformed with pCJ-MetZ-CL derived from *Chromobacterium violaceum*, in which the strain was fermented, and then recovered and disrupted according to the method disclosed in WO2008/013432. 0.05 mL of the enzyme was added. 0.02 mL of each mixture of methyl mercaptan and dimethyl sulfide at the different ratios was added to the prepared conversion reaction solution so as to initiate the enzyme reaction. Each solution was adjusted to contain the identical amount of methyl mercaptan. The reaction was performed at a temperature of 33° C. and 800 rpm for 1.0 min under stirring. For the termination of the reaction, a 0.2 N HCl solution was added to terminate the reaction. The concentration of the final product methionine was analyzed by HPLC. The results are shown in Table 4.

TABLE 4

Comparison of conversion rates of O-succinyl homoserine according to addition amount

| | Mixing ratio of methyl mercaptan:dimethyl sulfide (mol:mol) | | | |
|---|---|---|---|---|
| | 1:0 | 1:0.25 | 1:0.35 | 1:1 |
| Methionine [g/L] | 4.3 | 4.6 | 4.7 | 4.5 |
| Conversion rate [%] | 86 | 94 | 95 | 92 |
| Relative activity [%] | 100 | 109 | 110 | 107 |

As shown in Table 4, when the mixture of methyl mercaptan solution and dimethyl sulfide was added at a ratio of 1:0.35 (mol:mol), the activity was increased to approximately 10%, compared to the single use of methyl mercaptan. When the mixture of methyl mercaptan and dimethyl sulfide was added at a ratio of 1:0.25 and 1:1 (mol:mol), the enzymatic activity was not greatly increased, compared to the mixture ratio of 1:0.35 (mol:mol), but each of the enzymatic activity was increased to approximately 9% and 7%, compared to the single use of methyl mercaptan.

INDUSTRIAL APPLICABILITY

As described in the above Examples, the present invention provides a method of increasing conversion rate of methionine, thereby being applied to various fields including animal feeds, food additives, and medicines.

What is claimed is:

1. A method for producing methionine, comprising:
   1) preparing a reaction solution that includes a methionine precursor which is an O-acetyl homoserine or an O-succinyl homoserine, an enzyme which has the activity of converting the methionine precursor into methionine, and a mixture of methyl mercaptan and dimethyl sulfide; and
   2) performing an enzymatic conversion reaction while stirring the reaction solution.

2. The method for producing methionine according to claim 1, wherein the methyl mercaptan is a methyl mercaptan gas or a sodium methyl mercaptan solution.

3. The method for producing methionine according to claim 1, wherein a mixing ratio of methyl mercaptan and dimethyl sulfide is a ratio of methyl mercaptan:dimethyl sulfide of 1:0.05 to 1:1.

4. The method for producing methionine according to claim 3, wherein a mixing ratio of methyl mercaptan and dimethyl sulfide is a ratio of methyl mercaptan dimethyl sulfide of 1:0.20 to 1:1.

5. The method for producing methionine according to claim 4, wherein a mixing ratio of methyl mercaptan and dimethyl sulfide is a ratio of methyl mercaptan:dimethyl sulfide of 1:0.25 to 1:0.5.

6. The method for producing methionine according to claim 1, wherein the enzyme which has an activity of converting the methionine precursor into methionine is selected from the group consisting of cystathionine gamma synthase, O-succinyl homoserine sulfhydrylase and O-acetyl homoserine sulfhydrylase.

7. The method for producing methionine according to claim 1, further comprising terminating the enzymatic conversion reaction.

8. The method for producing methionine according to claim 1, further comprising a purification step of methionine which is produced by enzymatic conversion and contained in a reaction solution.

9. The method for producing methionine according to claim 8, wherein methionine purification step comprises:
   1) removing a microorganism from the enzymatic conversion reaction solution;
   2) decoloring and filtering the reaction solution, of which the microorganism is removed, to obtain a filtrate; and
   3) crystallizing from the filtrate.

* * * * *